United States Patent
Steinberg-Koch et al.

(10) Patent No.: US 12,224,070 B2
(45) Date of Patent: Feb. 11, 2025

(54) METHOD OF EVALUATING AUTOIMMUNE DISEASE RISK AND TREATMENT SELECTION

(71) Applicants: Predicta Med LTD, Herzliya (IL); Shlomit Steinberg-Koch, Tel Aviv (IL); Benjamin Getz, Ramat Hasharon (IL)

(72) Inventors: Shlomit Steinberg-Koch, Tel Aviv (IL); Benjamin Getz, Ramat Hasharon (IL)

(73) Assignee: PREDICTA MED LTD, Tel Aviv (IL)

( * ) Notice: Subject to any disclaimer, the term of this patent is extended or adjusted under 35 U.S.C. 154(b) by 118 days.

(21) Appl. No.: 17/596,015

(22) PCT Filed: Jun. 2, 2020

(86) PCT No.: PCT/IB2020/055206
§ 371 (c)(1),
(2) Date: Dec. 1, 2021

(87) PCT Pub. No.: WO2020/245727
PCT Pub. Date: Dec. 10, 2020

(65) Prior Publication Data
US 2022/0223293 A1 Jul. 14, 2022

Related U.S. Application Data

(60) Provisional application No. 62/856,067, filed on Jun. 2, 2019.

(51) Int. Cl.
*G16H 50/30* (2018.01)
*G16H 20/00* (2018.01)
*G16H 50/70* (2018.01)

(52) U.S. Cl.
CPC ............ *G16H 50/30* (2018.01); *G16H 20/00* (2018.01); *G16H 50/70* (2018.01)

(58) Field of Classification Search
None
See application file for complete search history.

(56) References Cited

U.S. PATENT DOCUMENTS

| 7,877,343 B2 | 1/2011 | Cafarella et al. |
| 8,068,993 B2 | 11/2011 | Karlov et al. |

(Continued)

FOREIGN PATENT DOCUMENTS

| WO | 2019055945 | 3/2019 |
| WO | 2019055945 A1 | 3/2019 |

OTHER PUBLICATIONS

Principle Component Analysis; Wikipedia (Year: 2024).*

*Primary Examiner* — John A Pauls
(74) *Attorney, Agent, or Firm* — Reches Patents

(57) ABSTRACT

Methods enabling prediction, screening, early diagnosis, and recommended intervention or treatment selection of autoimmune conditions using artificial intelligence operating in conjunction with large medical datasets. Logic is applied to historic population data to extract medical features and identify subjects with diagnosed autoimmune conditions, and the pre-diagnosis medical data is used to train a diagnosis classification algorithm. A self-supervised learning mechanism is separately used to generate a feature embedding transformation of the patients medical history into representational feature vectors. These patient feature vectors together with their expected diagnoses are used to train a multi-label classifier model using supervised learning. The embedding transformation and the multi-label classifier are then applied to a current subjects data to generate a patient diagnosis probability vector, predicting the existence of autoimmune conditions. These methods are applied to diagnose gastrointestinal autoimmune disorders using celiac disease as example.

37 Claims, 7 Drawing Sheets

(56) References Cited

U.S. PATENT DOCUMENTS

| | | | |
|---|---|---|---|
| 2004/0147840 A1* | 7/2004 | Duggirala | G06T 7/0012 600/437 |
| 2007/0020660 A1* | 1/2007 | Burczynski | C12Q 1/6883 435/6.17 |
| 2008/0131439 A1* | 6/2008 | Lois | A61K 31/4985 514/263.1 |
| 2012/0290324 A1* | 11/2012 | Ribbing | G16H 70/20 705/3 |
| 2017/0183732 A1* | 6/2017 | O'Connell | A61K 31/7052 |
| 2017/0306407 A1* | 10/2017 | Brefort | C12Q 1/6883 |
| 2018/0074038 A1* | 3/2018 | Fraser | G01N 33/6896 |
| 2019/0087727 A1 | 3/2019 | Skellenger | |
| 2019/0108912 A1* | 4/2019 | Spurlock, III | G06Q 10/10 |
| 2020/0303075 A1 | 9/2020 | Krishna et al. | |
| 2020/0342958 A1* | 10/2020 | McGovern | G16B 20/20 |

* cited by examiner

METHOD OF EVALUATING AUTOIMMUNE DISEASE RISK AND TREATMENT SELECTION

RELATED APPLICATION

This application claims priority from, and the benefit of, U.S. Provisional Application No. 62/856,067, filed 2 Jun. 2019, the contents of which are incorporated herein by reference.

FIELD

The present invention relates to the field of predictive medical diagnosis, especially for use in screening, early detection, and treatment selection of autoimmune-related conditions.

BACKGROUND

Autoimmune disease as a category affects 50 million Americans. It is one of the top ten causes of death in women under the age of 65, is the second highest cause of chronic illness, and is the top cause of morbidity in women in the United States. Additionally, autoimmune diseases have been reported to be on the rise in the U.S. and around the world, making this poorly understood category of diseases a public health crisis at levels comparable to heart disease and cancer. Because of a severe lack of awareness amongst the general public and medical practitioners and unequal allocation of research funding and focus at the National Institutes of Health (NIH), plus a lack of coordinated care and standardized diagnostic tests, the associated cost of autoimmune diseases has become a significant portion of the rising cost of healthcare in the U.S.

There are 100+ known autoimmune diseases, all caused by a common thread which is the autoimmunity process. The autoimmunity process is initiated when one's immune system becomes overactive and, rather than destroy invader cells, such as infections and viruses, targets one's own healthy cells and tissues causing various autoimmune diseases. Autoimmune diseases can affect any system in the body. Nearly any body part can be involved. The symptoms vary widely among the various types and in-between different subjects, making the autoimmune diseases difficult to diagnose. Common symptoms include low grade fever and feeling tired. Some autoimmune diseases have a hereditary component, and certain cases may be triggered by infections or other environmental factors. Common diseases that are generally considered autoimmune include celiac disease, diabetes mellitus type 1, Graves' disease, inflammatory bowel disease, multiple sclerosis, psoriasis, rheumatoid arthritis, and systemic lupus erythematosus.

Providing the correct treatment for an autoimmune disease is a complex puzzle. To obtain proper treatment, subjects must visit a wide variety of specialties within medicine. Because autoimmune diseases affect multiple organs and systems in the body, teams of physicians ranging from rheumatologist, ophthalmologist, neurologist, and gastroenterologist often are needed to treat symptoms of an individual subject. This method of treatment is time consuming and often fiscally wasteful as there is typically no model for proper coordinated care amongst medical systems and physicians, needed to enable adequate monitoring, diagnostic testing and prescription drug treatments. Also, the addition of new cutting edge biologic treatments for autoimmune patients requires an even higher level of coordination and expertise from physicians as these treatments, while revolutionary as lifesaving and quality of life-enhancing tools, must be heavily monitored for short-term and long-term adverse side effects and dosage issues.

One of the most prevalent autoimmune diseases, which usually takes multiple years to diagnose is celiac disease (CD; also known as coeliac disease, celiac sprue, non-tropical sprue, and gluten-sensitive enteropathy). Celiac disease is a multifactorial, autoimmune enteropathy characterized by gluten sensitivity and diverse clinical features, which may develop over many years. Contributing factors to the development of a clinical diagnosis of celiac disease comprise genetic, immunological and environmental factors. The genetic influence is primarily derived from two of the many human leukocyte antigens (HLA), specifically alleles DQ2 and DQ8. CD damages the villi of the small intestine and interferes with absorption of nutrients from food. According to recent research, the worldwide prevalence of celiac disease is 1.4% based on serologic (blood) testing, while 83%-95% of these patients remain undiagnosed. An estimated 1 in 133 Americans, or almost 1% of the population, has celiac disease (affecting men and women of all ages and races). It is estimated that over 80% of Americans who have CD are undiagnosed or misdiagnosed with other conditions. This means that about 2.4 million individuals in the US suffer with signs and symptoms of CD without a diagnosis and thus without targeted treatment. The time a person with celiac waits to be correctly diagnosed is on average 6-10 years. A recent study found that the mean delay to diagnosis from the first symptoms was 9.7 years, and from the first doctor visit, 5.8 years. The celiac disease diagnosis rate by 2019 was estimated to reach only 50-60%. The cost reduction in early detection of celiac can potentially save billions of dollars to the American health care system.

Delay in CD diagnosis can lead to a number of other disorders including infertility, reduced bone density, neurological disorders, some cancers, and other autoimmune diseases. A study published in 2009 yielded two major findings—first, undiagnosed CD was associated with a nearly 4-fold increased risk of death compared with subjects without serologic evidence of CD. Second, the prevalence of CD appears to have increased dramatically in the United States during the past 50 years. Over a four-year period, people with undiagnosed CD cost the health care system approximately $4,000 more than healthy individuals.

Early detection can be challenging: Both diagnostic rates and diagnostic delays show that celiac disease has a low rate of suspicion on clinical grounds. Two contributory factors in the difficulty of CD diagnosis are that the gastrointestinal symptoms may overlap with those found in other disorders, and that in some individuals the gastrointestinal component is mild or even mostly absent. On the other hand, the implications of late/delayed diagnosis are significant. Untreated CD results in poor Health-Related Quality of Life (HRQoL), a score that is improved relative to that of the general population if an individual with CD is diagnosed and treated. By shortening the diagnostic delay, it is possible to reduce this unnecessary burden of disease. The mean quality-adjusted life year (QALY) score during the year prior to initiated treatment was 0.66; it improved after diagnosis and treatment to 0.86, which was then better than that of the general population (0.79).

Currently, for most children and adults, the best way to screen for celiac disease is with the tissue transglutaminase IgA (TTG-IgA) antibody. In order to render the celiac disease test accurate, sometimes a gluten challenge is administered to ensure that the subject generates enough of the TTG-IgA antibody. Sensitivity rate for this test is 98% and specificity is 95%. Because of potential for false antibody test results, a biopsy of the small intestine is the only definite way to diagnose celiac disease.

Markov modeling suggests that, given the mortality associated with untreated symptomatic celiac disease, targeted screening may be cost effective in areas of moderate to high prevalence. Screening would involve performing the blood test for TTG-IgA in any individual suspected of having CD. Whereas this effort would entail a significant cost and give false-negative results in 2% of cases, even despite increased awareness in society and in health care, many CD cases would be missed in a screening campaign due to vague or atypical symptoms. Another possible suggested option is mass screening for CD. CD mass screening fulfils most of the listed criteria for a medical mass screening adapted by WHO from the 1968 classic guidelines on disease screening by Wilson and Jungner. It was recently estimated in the United States that the medical cost for clinically detected CD patients is reduced by close to $1800 the year following diagnosis as compared to the average cost during the preceding years.

Aside from CD, other autoimmune related gastrointestinal disorders cause significant morbidity and also have a rate of delayed diagnosis in the general population. Inflammatory bowel disease (IBD) has two major forms: Crohn's disease (CD) and ulcerative colitis (UC). The incidence of CD in North America is about 3.1-20.2 per 100,000 human years and has a prevalence of 201 per 100,000 individuals in the population. Ulcerative colitis is one of the two type of IBD which plagues up to 1.4 million individuals in the US alone. A third related disease is nonalcoholic steatohepatitis (NASH), creating an overwhelming combined burden of illness on the healthcare system in the United States alone. It is estimated that the current costs associated with NASH and its associated sequelae will top $100 billion in annual direct medical expenditure.

Currently, only serology and blood tests are being used to detect and predict CD, which, while acceptably effective, are inconvenient methods, such that potential sufferers may forego the tests, and not be diagnosed correctly. There also exist a number of prior patents and patent applications in the field of using algorithms for the diagnosis of celiac and other diseases as listed below:

EP 2,367,561 Compositions and methods for treatment of celiac disease

U.S. Pat. No. 6,074,835 Diagnosis, prevention and treatment of ulcerative colitis, and clinical subtypes thereof, using Histone H1

U.S. Pat. No. 9,474,490 Methods and systems of evaluation a risk of a gastrointestinal cancer U.S. Pat. No. 9,703,929 Method and system for microbiome-derived diagnostics and therapeutics U.S. Pat. No. 9,754,383 Automated methods for assessment of celiac disease WO 2010/030929 Methods and systems for incorporating multiple environmental and genetic risk factors US 2010/094560 Methods for diagnosing irritable bowel syndrome US 2014/051594 Methods for diagnosing irritable bowel syndrome US 2019/0108912 Method for predicting and detecting disease US 2018/0321259 Pathway specific markers for diagnosing irritable bowel syndrome However, these methods may be considered by some to be either limited in scope, or of limited effectiveness or convenience, such that there still exists a need for a more comprehensive solution for the screening and early diagnosis of gastrointestinal-related diseases which also provides a method to provide a treatment plan and thus overcomes at least some of the disadvantages of prior art systems and methods.

The disclosures of each of the publications mentioned in this section and in other sections of the specification, are hereby incorporated by reference, each in its entirety.

SUMMARY

The methods of the present disclosure are based on the ability to cluster individuals or groups of individuals based on defining characteristics, such as demographic, symptoms, lab test results, medications, procedures, biomarkers, or other measurable properties, while recognizing that individuals differ in an almost infinite number of characteristics representing their biologic individuality. The methods of the present disclosure collect, store, and analyze huge bodies of data to classify people according to their individual likelihood of acquiring symptoms of a specific autoimmune disease or having a specific autoimmune disease which is undiagnosed at the point of the data collection.

Because most autoimmune diseases develop over time, during which affected individuals are clinically asymptomatic, and because genetic markers of heightened inherited susceptibility can be measured in genome-wide association studies long before symptoms are noticed, identifying potential patients at an asymptomatic stage provides an opportunity to initiate preventive measures and minimize late-phase interventions which are primarily ineffective after irreversible tissue damage has occurred. Taken together with immunologic and biochemical markers, genomic markers can indicate that a potentially damaging autoimmune process is in process long before symptoms occur, at a stage when intervention has a higher likelihood of preventing long-term damage.

The present disclosure describes new exemplary methods for predicting the risk in potential or latent patients, of the presence or the evolution of an autoimmune disease, using CD as an exemplary disorder. The method provides a screening recommendation for the general population according to relative risk, enables early diagnosis, and assists in formulating a treatment plan and disease management. The present disclosure describes a decision support platform, using artificial intelligence (AI) techniques such as machine learning, deep learning, and natural language processing (NLP) to enable early detection and personalized treatment selection. Information may be collected from the internet of things (IoT), a system of interrelated computing devices, mechanical and digital machines, objects, animals or people that are provided with unique identifiers and the ability to transfer data over a network without requiring human-to-human or human-to-computer interaction.

The novel algorithms of the present disclosure process a collection of subject data collected from sources comprising at least some of electronic medical records (EMR), electronic health records (EHR), insurance claims data, patient sensors data such as IoT sensors, or data from health application programs, and suggest a subject's risk for having a common or uncommon autoimmune related disease, such as CD, IBD (Crohn's disease/ulcerative colitis), multiple sclerosis (MS), rheumatoid arthritis (RA), systemic lupus erythematosus (SLE), and others. The method prioritizes subjects according to probability/risk and makes recommendations regarding the appropriate subsequent steps, such as related tests or prescription of a specific treatment. The system provides explanatory output regarding relevant symptoms and signs, and analyzes trends, symptom recurrence, symptom distribution and all relevant patient history, to determine the risk of the particular subject having or developing the specific disease under consideration by the system. The service enables providers to seamlessly integrate this solution into their current workflow by either integrating the algorithms and software into the existing EMR system or by providing a separate software interface.

The present disclosure describes a method of evaluating risk for autoimmune disease risk, such as CD, inflammatory bowel disease, ulcerative colitis, MS, RA, SLE, and other autoimmune related disorders. One exemplary method comprises the steps of:
 i) collecting medical data of subjects in a target population, comprising a set of features such as symptoms, blood test results, other lab tests, diagnostics, medications, biomarkers and measurements as collected,
 ii) providing at least one classifier, which may be a multi-label classifier, that has been trained on a large population dataset to diagnose at least one specific autoimmune disease such as CD, these classifiers are trained and tested on a large set of sample subjects; a collection of symptoms; concurrent diagnoses; or other parameters, and includes some subjects with a diagnosis of CD or other autoimmune related diseases mentioned above who were previously diagnosed by traditional means, and
 iii) applying the algorithmic classifier to individual subjects' data collection, resulting in the probability of the target individuals having CD (or any of the other autoimmune related diseases).

In some embodiments of the present disclosure, imaging processing is used to correlate the small intestinal biopsy results to the predictive model. Intestinal biopsy provides tissue for microscopic analysis of the intestinal villi, revealing signs not only of current severe disease, but in subjects predicted by the model to have a high risk of developing or having CD, also about the potential and latent celiac population. These predictions are based on milder microscopic changes, such as inflammation, loss of villi height, or inflammatory cell infiltration, in the intestinal tissue.

The method may also predict the risk of a given subject to develop CD or any other autoimmune related disease in the future. For example, given the genetic predisposition of individuals with specific white blood cell markers, i.e., human leukocyte antigens (HLA) alleles DQ2 and/or DQ8, to develop CD, first degree relatives of such individuals are at higher risk of developing the disease compared with the general population. Finally, the method provides an option for personalized treatment selection according to the target individual's clinical presentation and data related characteristics. The method follows the subject's medical data throughout therapy and classifies the individual response to each treatment. Over time, the algorithm classifies each individual according to other individuals with the same feature patterns and their responses to each treatment. This provides an opportunity for new subjects to be introduced into the appropriate classification, starting the optimal treatment immediately. Thus, the system allows for personalized care and treatment selection based on subjects' clustering and similarities.

The present disclosure reveals an AI-based decision support platform which analyzes subjects' data from multiple sources such as EMR, EHR, claims data, sensor data, or health application data, and calculates a risk factor (probability) for having autoimmune related disease, examples of which may be CD, IBD, MS, RA, SLE and others. The method is focused on helping healthcare providers identify autoimmune related illnesses in undiagnosed subjects as early as possible and select the best treatment for these patients.

The platform can be integrated into the EMR system and thus perform several functions. Firstly, it raises an alert through the EMR regarding subjects with a risk factor above a pre-selected or automatically determined threshold, and based on that alert the doctor can summon the individual for further examination or, using the system, send the individual for follow up tests. Another option is that the health insurance provider will use the system via the care manager, or other individual in a position of managing business operations and patient care, and send requests for the providers to further examine specific individuals or summon the individual for further examination at his doctor's office or, using the system, send the individual for follow up tests. Secondly, the system provides the doctor with all the disease-relevant data and recommended actions to have a full clinical picture during visits of patients whose evaluations have superseded the threshold of probability for having CD. Thirdly, it provides the users with a customizable interface which tracks all subjects at risk, prioritizes them and includes information about their risk factor, symptoms, recommended future examinations, etc. The current method thus provides a solution for both symptomatic and atypically symptomatic subjects, of which the latter are especially hard to diagnose due to the non-gastrointestinal nature of their symptoms. The method has a built-in flexibility, such that HMO policy makers or health care providers can set a policy determining the desired ratio of false positive:false negative outcomes, affecting the cost-benefit ratio of the HMO. This policy is made by setting a threshold for the risk factor, above or below which subjects are called into the clinic to be further examined and diagnosed.

The presently disclosed system uses AI-based methods employing machine learning, deep learning, NLP techniques, and other advances learning methods trained on data acquired from multiple data sources such as EMRs, EHRs and claims data. Training the method entails building a mathematical model based on sample data, known as "training data", in order to enable the algorithmic method to make predictions or decisions without being explicitly programmed to do so. The system takes into account both structured data, which is highly-organized and formatted to be searchable in relational databases, and unstructured data, which could have no pre-defined format or organization, making it much more difficult to collect, process, and analyze. The trained algorithmic method synthesizes the data and outputs a risk factor for each individual in the target population. EMR-specific modular computer plugins are used to connect between the EMR-specific data sources provided by the health care provider and the platform-agnostic algorithmic system of the present disclosure. The presently disclosed algorithmic system then provides alerts and analytics data through the EMR's application programming interface to doctors and policy makers. With the AI component used to train the algorithm, accurate performance and predictive value of the system increases over time, as more patient data becomes available for processing.

Several advantages of the presently disclosed system and method are now listed. The method is dedicated to and focused on autoimmune diseases, leading to a deep understanding of these specific diseases. Proprietary data are generated through research of both symptomatic and asymptomatic individuals. This data collection will fill a current void of information regarding these subjects due to many of them being undiagnosed. Further, the data derived from these analyses may be made available to other entities focusing on the development of treatments for autoimmune diseases, such as pharmaceutical companies. The system may be integrated into the current workflow of health management systems.

The current description uses celiac disease and related gastrointestinal conditions as a model for showing how the disclosed method operates, although systems and methods of this disclosure relate to every autoimmune disease. Such systems provide a comprehensive solution for early CD diagnosis and treatment formulation, based on EMR/EHR/claims/IoT-sensors/health-app data analysis via machine/deep learning/NLP and other advanced learning techniques. Further, this platform can be tailored for screening, diagnosis and providing a treatment plan of other systemic diseases.

A summary of steps followed in an exemplary implementation of the methods comprises:

1) Generating training data for a machine learning/deep learning diagnosis algorithm from a large database of historical medical data of a general population, where each subject's file is tagged with diagnosed gastrointestinal autoimmune diseases, if those exist, and the medical history data prior to such diagnosis is separated, pre-processed and combined with the actual diagnosis as the target output for the diagnosis algorithm. The selection of patient files and identification of their diagnosis procedure and actual diagnosed conditions is performed using expert medical logic related to such condition.

2) Generating, using self-supervised representation learning, a feature embedding transformation that converts the input medical history parameters and data into a vector of real numbers in a way that encapsulates a compact representation of data that influences the diagnosis algorithm, such that patients with similar conditions and symptoms will transform into similar vectors.

In this application, and in machine learning, the term "vector" can be understood to cover any of the suggestions relating to the designation of data for transfer within an algorithmic process. Whereas a vector is a one dimensional array of numbers, a vector array is a multi-dimensional sequence of real numbers.

3) Transforming the selected patient files from step 1 using the feature embedding transform developed in step 2 and combining the output vectors with the target diagnosis to generate a database of training vectors.

4) Training a multi-label classifier model, using training database from step 3. The classifier maps a patient medical feature vector into a diagnosis probability vector that provides likelihood of a subject having the specified gastrointestinal autoimmune disease. The training cycles continue until adequate accuracy is reached.

5) Using classifier model from step 4, to identify and diagnose patients from the population that have high likelihood of having a yet undiagnosed disease or high likelihood to develop such condition.

A summary of a further exemplary implementation of the disclosed methods to the diagnosis of celiac disease comprises processing each individual's medical data set by the following steps:

(i) turning string-type data points into categorical data,
(ii) annotating every missing or censored data point,
(iii) allocating all missing or censored data points the median of non-missing data points for the relevant subpopulation,
(iv) creating a full data set for each individual,
(v) training said algorithm based on said full data sets,
(vi) providing a probability that a given individual will have a positive tTG-IgA test,
(vii) validating said algorithm on a new data source,
(viii) choosing best hyper-parameters based on validated data sets, and
(ix) performing final evaluation on validated data sets.

An additional summary of an exemplary implementation of the disclosed methods comprises:

(i) collecting and inputting data derived from at least one of electronic medical/health records, sensors data (e.g. IoT sensors) or health app data and medical claims from individuals,
(ii) combining or collecting medical data sets from a group of individuals into an aggregated data source,
(iii) preparing and processing said individuals' medical data to extract pre-defined relevant parameters for any of diagnosis, screening, and prediction of celiac disease,
(iv) if one or more said relevant parameters is missing from an individual's medical data set, deriving average values for said missing relevant parameters from said data source,
(v) using said data source to train an algorithm for predicting celiac disease diagnosis,
(vi) running said algorithm on data sets from individuals to calculate a probability of each individual having a diagnosis of celiac disease,
(vii) providing an alert when the probability for a given individual exceeds a predetermined threshold, and
(viii) providing guidelines for at least one of treatment selection and disease management.

There is thus provided in accordance with an exemplary implementation of the systems and methods described in this disclosure, a method for predictive diagnosis of at least one autoimmune disease in a subject, comprising:

(i) applying to health related data of the subject, a machine learning method adapted to convert parameters of the health related data, some of which may be indicative of a diagnosis of an autoimmune disease, into a vector that provides a compact representation of the health related data that reflects a medical condition of the subject, and
(ii) applying a classifier model to the vector generated in step (i) to identify whether the medical condition of the subject indicates a likelihood of the subject having or developing an autoimmune disease, wherein the classifier model is generated by:
(iii) accessing a database comprising records of health related data of a large population,
(iv) tagging at least most of the records with information indicating if a member of the large population with whom a record is associated, has been diagnosed with an autoimmune disease,
(v) performing the machine learning method on at least some of the tagged health related records, to convert tagged records into target diagnosis vectors indicating that the member associated with the tagged record has been diagnosed with an autoimmune disease,
(vi) training the classifier model iteratively to relate features of each target diagnosis vector with a previous diagnosis of an autoimmune disease by correlating parameters of the tagged records representing features of an autoimmune disease for the member associated with that record, and (vii) repeating the training until the correlation of parameters with the diagnosis of an autoimmune disease shows a desired level of accuracy, such that application of the classifier model to the vector generated in step (i) predicts with the desired level of accuracy, the likelihood that the subject has an autoimmune disease.

In any such methods described in this disclosure, it is to be understood that the term predictive diagnosis is intended to cover also methods of screening for an autoimmune disease, or early detection of an autoimmune disease, or similar terms intended to relate to the determination of such a disease, whether present or whether expected to be present on the basis of the implementation of the methods.

Furthermore, in any such methods, the autoimmune disease may be at least one of a gastrointestinal autoimmune disease such as celiac disease, ulcerative colitis, or Crohn's disease. Additionally, the classifier model may be trained to predict a diagnosis of either a specific autoimmune disease or any autoimmune disease. The multi-class classifier model may also be developed using supervised learning, in which case, the supervised learning uses a form of artificial intelligence.

In such methods, the machine learning method may be developed using self-supervised representation learning. In such a case, the self-supervised representation learning may use a form of artificial intelligence.

According to further exemplary implementations of the methods of the present disclosure, the database may comprise historical data on a subpopulation of subjects having a diagnosis of an autoimmune disease. Additionally, in any such methods, tagging the records may be performed using expert medical logic.

Furthermore, in any of the above described methods, a database comprising records of health related data of a large population may be used to generate the machine learning method. The same database may be used for generating both the machine learning method and the classifier model.

In yet further implementations of the present methods, the predicted diagnosis of an autoimmune disease in the subject may be validated by a health practitioner.

Furthermore, the health related data of the subject may be tagged and added to the database comprising records of health related data of the large population. In that case, feedback from the health practitioner may be appended into the expert medical logic to improve accuracy of the predictive diagnostic method.

According to yet further implementations of the presently described methods, the parameters may be defined by current legacy methods based on a least one of published medical literature, diseases registries, medical practice guidelines and the medical data. Additionally, the health-related data may comprise at least some of electronic medical or health records, the internet of things or other sensor data, health application data, and data from medical claims.

Furthermore, training the classifier model may be performed using at least one of artificial intelligence, machine learning, deep learning, natural language processing, reinforcement learning, and big data analytics techniques. The classifier model may be a multi-label classifier model that outputs multiple results associated with the likelihood of the subject having more than one specific type of autoimmune disease or autoimmune related disease.

Any of the previously described methods may further comprise using supervised learning, training an intervention recommendation model to provide at least one of recommended intervention, treatment selection, disease management recommendations, and decision support guidelines. In any of those cases, the intervention recommendation model may be trained by supervised learning from at least one of either the success or the effectiveness of interventions and treatments in the database comprising records of health related data of a large population.

In all such methods, the subject may belong to a subpopulation of the large population whose records of health related data comprise the database. Additionally, the health related data of the large population database may be preprocessed by standardizing, marking and filling missing data points, and normalizing inputs. In that case, the health related data of the large population database may be used to create self-supervised training data. In the latter case, the training data may be used to train the machine learning method used to create embedding vectors that are a compact representation of the input semantics and context.

According to yet further exemplary methods, the health related data of the large population database may be standardized by turning string-type data into categorical data. Missing data may be handled by identification, marking, and filling in absent data points as actual data. In such a situation, absent data points may be allocated a median value, and the statistical distribution of continuous data is then normalized.

In further exemplary methods, optimal hyper-parameters may be chosen and exported based on model test results on validation data. Additionally, the machine learning method may be a feature embedding transformation. Likewise, the tagging of the records may also be performed with information indicating with which autoimmune disease the member has been diagnosed.

In any of the above described methods, the application of the classifier model to the generated vector may predict with the desired level of accuracy, not only the likelihood that the subject has an autoimmune disease, but also that the subject may have a specific autoimmune disease.

Any of the previously described methods may further comprise applying an intervention recommendation model to the patient diagnosis probability vector, if the subject is identified as having greater than a pre-defined likelihood of having or developing an autoimmune disease, wherein the intervention recommendation model may be generated by:
a) accessing a database comprising records of health related data of members of a large population,
b) using expert medical logic to determine most effective treatment and follow up parameters of members of the large population who have been previously diagnosed with and treated for an autoimmune disease, and
c) training the intervention recommendation model iteratively to provide model parameters that meet accuracy requirements on test inputs, the model parameters provided by the intervention recommendation model being applied to the health related data of the subject and the patient diagnosis probability vector, to generate recommended interventions.

There is further provided according to a further implementation described in the present disclosure, a method of determining the presence of an autoimmune disease in a subject, the method comprising:
(i) aggregating health related individual data sets of the subject, into a personal data store associated with the subject, (ii) applying to the aggregated health related data of the subject, a machine learning method for converting parameters of the health related data, some of which may be indicative of a diagnosis of an autoimmune disease, into a vector that provides a compact representation of the health related data that reflects a medical condition of the subject, (iii) applying a classifier model to the vector to calculate the probability of the subject having an autoimmune disease or developing an autoimmune disease, wherein:

(iv) if the probability exceeds a predefined threshold, inputting the vector and the health related data of the subject into an interventional recommendation model for outputting initial recommendations for an intervention or a treatment option selected from a group of potential interventions or treatments, and (v) using a method previously trained by a machine learning routine including access to novel treatments, providing an assumed optimum treatment for long term management of the autoimmune disease, and (vi) if the probability does not exceed a predefined threshold, adding retrospective feedback from medical personnel to the health related data of the subject and returning to step (iii).

In such a method, the classifier model may be applied to the vector to calculate the probability of the subject either having a specific autoimmune disease or developing a specific autoimmune disease.

There is also provided according of yet another implementation of such methods, a method for providing recommendations on at least one of intervention, treatment, or disease management for an autoimmune disease, comprising:

i) collecting health related data of a subject and applying thereto, a machine learning method capable of converting parameters of the health related data, some of which may be indicative of a diagnosis of an autoimmune disease, into a vector that provides a compact representation of the health related data reflecting a medical condition of the subject, ii) applying a classifier model to the vector generated in step i) to generate a patient diagnosis probability vector that indicates a likelihood of the subject having or developing an autoimmune disease, iii) if the subject is identified as having greater than a pre-defined likelihood of having or developing an autoimmune disease, applying an intervention recommendation model to the patient diagnosis probability vector generated in step ii), wherein the intervention recommendation model is generated by:

a) accessing a database comprising records of health related data of members of a large population, b) using expert medical logic to determine most effective treatment and follow up parameters of members of the large population who have been previously diagnosed with and treated for an autoimmune disease, and c) training the intervention recommendation model iteratively to meet the recommendation accuracy requirements, wherein the generated intervention recommendation model is applied to the health related data of the subject and to the patient diagnosis probability vector generated in step ii), to generate recommended interventions.

In the latter described method, the recommended interventions may comprise at least one of a ranked list of follow up and treatment recommendations for drugs or other chemical therapies, referrals to specialists, schedule of follow up testing, and health-promoting activities including diet or exercise. In either of these two mentioned methods, the autoimmune disease may be at least one of a gastrointestinal autoimmune disease such as celiac disease, ulcerative colitis, or Crohn's disease.

In any of the last described methods for providing recommendations, the classifier model may be trained to predict a diagnosis of either a specific autoimmune disease or any autoimmune disease. The database may comprise historical data on a subpopulation of subjects having a diagnosis of an autoimmune disease, or it may comprise records of health-related data of a large population is used to generate the machine learning method. Furthermore, the intervention recommendations may be validated by a health practitioner, and feedback from the health practitioner may be appended into the expert medical logic to improve accuracy of the intervention recommendation model.

Additionally, in these methods, the health related data of the subject may tagged and added to the database comprising records of health related data of the large population. The health related data may comprise at least some of electronic medical/health records, internet of things or other sensors data, health application data, and data from medical claims. Training the intervention recommendation model may be performed using at least one of artificial intelligence, machine learning, deep learning, natural language processing, reinforcement learning, and big data analytics techniques. The intervention recommendation model may be a form of artificial intelligence algorithm trained using supervised learning. Alternatively, the intervention recommendation model may be trained via supervised learning from the success or effectiveness of interventions and treatments in the database comprising records of health related data of a large population.

According to further such methods, the classifier model may be a multi-label classifier model that outputs multiple results associated with the likelihood of the subject having at least one specific type of autoimmune disease or autoimmune related disease. The subject may belong to a subpopulation of the large population whose records of health related data comprise the database. Finally, the machine learning method may be a feature embedding transformation.

There is further provided, according to other implementations in the present disclosure, a system for predictive diagnosis of at least one autoimmune disease in a subject, comprising:

i) at least one processor comprising a controller adapted to run at least one of artificial intelligence algorithms, and training and inference logic, ii) a memory adapted to enable the processor to access expert medical logic and at least one of patient feature vectors and patient diagnosis probability vectors stored on the memory, and iii) at least one type of data storage adapted to contain records of health related data of a large population, classifier model parameters, and embedding model parameters derived from the training of the artificial intelligence algorithm by the processor, wherein the at least one processor is configured to:

a) apply the expert medical logic to the health related data to produce updated patient feature vectors and patient diagnosis vectors, b) generate classifier model parameters based on algorithm training to process the feature vectors, c) input the classifier model parameters into an embedding model to classify the patient diagnosis vectors, and d) output the likelihood of a predictive diagnosis of at least one autoimmune disease in the subject.

In such a system, the processor may be further configured to provide at least one of recommended interventions, referrals to specialists, schedule of follow up testing, and a ranked list of treatment recommendations. Additionally, the artificial intelligence algorithms may comprise a machine learning algorithm or a deep learning algorithm.

Such systems may further comprise a user interface that provides to a human operator at least one of recommended interventions, referrals to specialists, schedule of follow up testing, and ranked list of treatment recommendations. Additionally, the recommended interventions may include health-promoting activities such as diet or exercise, and treatment recommendations may include drugs or other chemical therapies.

BRIEF DESCRIPTION OF THE DRAWINGS

The presently claimed invention will be understood and appreciated more fully from the following detailed description, taken in conjunction with the drawings in which:

DETAILED DESCRIPTION

Figure 1:
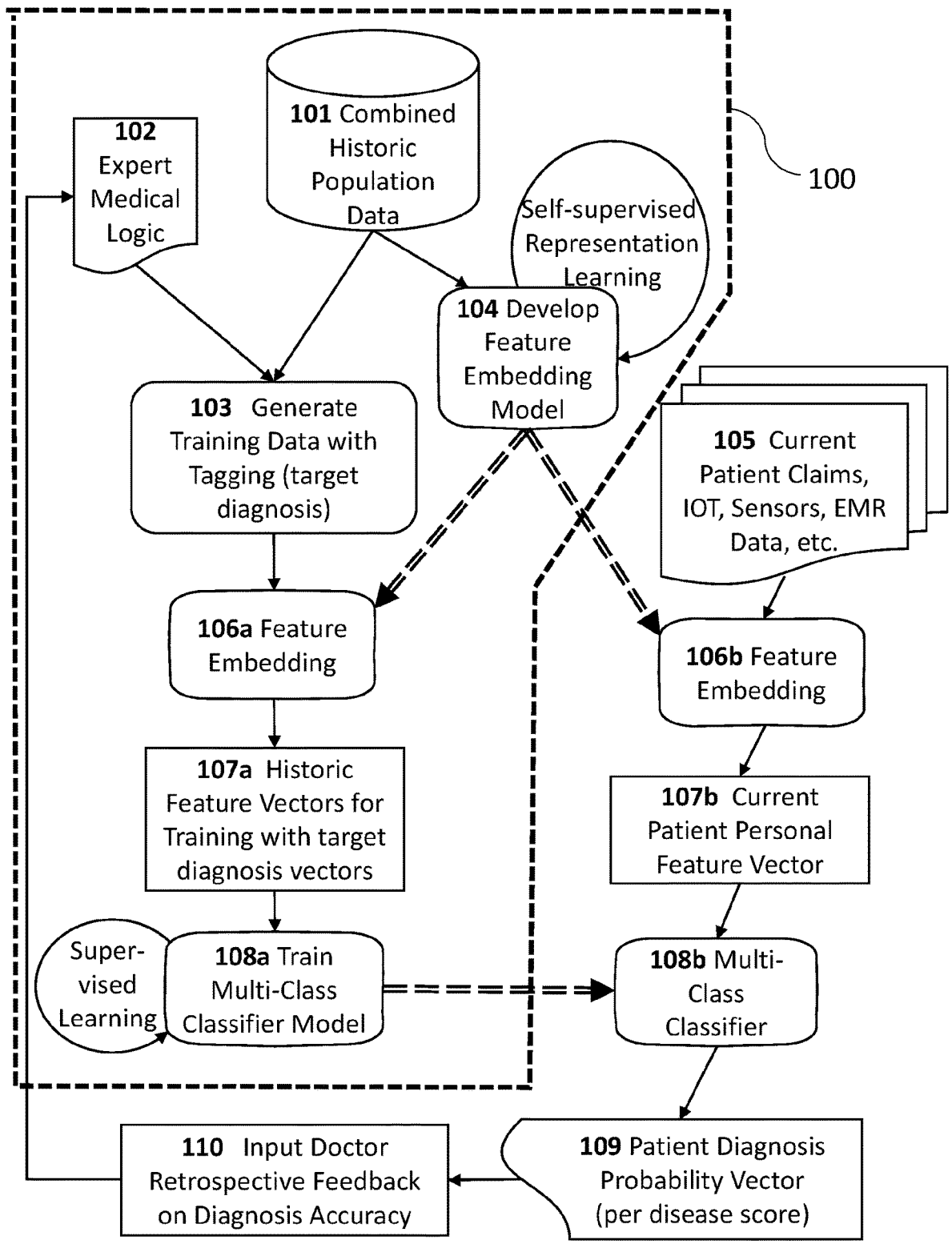
FIG. 1 depicts the flow and processing of information for diagnostic, screening or decision support purposes in an exemplary implementation of the methods of the present disclosure.

Reference is first made to FIG. 1, which illustrates schematically the overall structure of an exemplary implementation of the disclosed invention. A method detects individuals having characteristics that indicate a specific disease process. In a first phase of the method, historical patient data from electronic medical records (EMR), electronic health records (EHR), claims data or data from other sources are collected, followed by application of machine/deep learning, natural language processing (NLP), or other individual or combined machine learning techniques to train an algorithm of the method to identify subjects with the autoimmune conditions which are to be diagnosed based on known cases of such disease in the historic population data. In a second phase, new patient data are input to the algorithm to enable determination of the probability and risk that a given individual in the new population has an autoimmune condition. Specifics of this process are delineated for an exemplary implementation of the method: in the example provided here, the method determines the probability of a given individual having celiac disease or another gastrointestinal autoimmune disorder, either currently or predicted to develop within a future time frame.

In block 101, a historic database of insurer medical claims and/or EMR data for a large population, representing the target population for this algorithm, is accessed to provide examples for training the models of the system. This data is augmented with additional sources, such as IOT sensor data, subject provided information, and aggregated statistics relevant to target subjects collected either from research datasets, or via use of the proposed system. This information is used in subsequent steps 103 and 106a to generate processed and filtered training information, ultimately for use in step 109.

In step 103, the large population data from block 101 is used in combination with rules derived from medical experts or known medical protocols, here referred to as "expert medical logic" 102, to generate tagged or labeled training data of subjects. Expert medical logic, entered into the system, is a database of rules providing specific logic how to classify subjects retrospectively, based on the data provided. This logic is based on interviews with medical doctors and information collected from research papers that enable the system to classify retrospectively who has been diagnosed with which diseases, so that this classification can be used to train the artificial intelligence classifier. Data tagging, in the context of this application, is the process of classifying and tagging data samples to label the historic population data with the target autoimmune diagnoses. The system uses the expert medical logic to retroactively identify and label each person's medical history with the autoimmune conditions that he has been later positively diagnosed with. The data is separated and a tag assigned to it prior to the diagnosis. The tagged training data will be used in subsequent steps to learn how to classify and predict the risk of having such conditions via analyzing patient data prior to the diagnosis.

In step 104, the large dataset of patient files is utilized to train a "feature embedding model". The feature embedding model is a machine learning transformation that converts the patient data into a finite vector of real numbers. The vector space is of lower dimension than the entire patient data and therefore compresses the data keeping the important aspects and features that enable subject classification and diagnosis but also makes similar patients convert into vectors with a small distance between them. This transformation generates a representation of the data that is easier to classify and can better classify new subjects it has not seen before. This method is known as self-supervised representation learning and is used to generate an embedding model and optimize its parameters. Supervised learning and self-supervised representation learning are two different deep learning mechanisms. Supervised learning uses many classified examples to train the algorithm to correctly classify new samples based on multi-variate similarity to the training samples. Self-supervised learning is unsupervised learning in which the algorithm is trained to identify key differentiating features between classes of subjects, by going over many unclassified patient medical data files and studying the relationship between different segments or views of the medical files presented to it.

In this application, the embedding layer is a low-dimensional space for creating a dense encoding that represents the subject's medical history. This model is trained and generated using self-supervised learning and optimized over a large training set of historical medical data collected from a large population in step 101. The embedding for autoimmune disease diagnosis captures the semantics of the input from step 101, e.g., a variety of background data, comprising both medical data, environmental conditions, and patient risk factors, by placing semantically similar inputs close together in the embedding space. Although the embedding model itself may be reused among various populations, the subject population to which the method will be applied in steps 106b to 109 should be similar to, or derived from, the larger general population in block 101, such that the embedding parameters accurately distinguish among healthy individuals and those with a specific autoimmune diagnosis in that population. This is important because normal ranges of lab values and ways in which autoimmune conditions appear may differ among various populations. The embedding model parameters generated in step 104 are then input to step 106a to embed the tagged training data. The relevant patient data features selected for training are defined by current legacy methods, based on at least two of published medical literature, diseases registries, medical practice guidelines and the medical data.

In step 106a, the tagged history data of all of the recorded subjects, is passed through the feature embedding mechanism, loaded with the model derived in step 104, and is then converted into tagged feature vectors for training 107a.

In step 108a, a multi-output classifier model is trained using supervised learning of the tagged training data (107a). The steps 101 to 108a, shown in FIG. 1 within the dotted line 100, are steps used for the periodic training of the artificial intelligence models using the large historic population data. Steps 106b to 108b, on the other hand, are steps in which the feature embedding and classifying of the subject data are applied to the data of the currently analyzed patients, whose diagnoses are being resolved.

The output from step 108a comprises multi-label classifier model parameters, which are also used to classify current patient data vector 107b in step 108b. Multi-label classification is a classification mechanism that outputs multiple results associated with the likelihood of the inspected object being of a specified class. The classifier classifies object into multiple classes based on the input features of the object. In the context of this disclosure, the classifier provides probabilities of the analyzed person having: any autoimmune disease, any gastrointestinal autoimmune disease, or a specific autoimmune disorder, based on features found in his collection of medical records and data.

The embedding model parameters output from the self-supervised learning in step 104 are also used as input model for step 106b. Additional input for step 106b comprises raw data on a current subject's present situation and recent history from a variety of sources. The raw data may comprise at least some of patient insurance claims, electronic medical record data, and information gleaned or acquired from IoT, sensors, and health app data 105. In this step, the system applies the embedding parameters developed in step 104 to the raw data from block 105 and the output is a personal feature vector 107b representing the data of the current subject. This output is then used as the input for the multi-label classifier model of step 108b.

In step 108b, the model parameters developed in 108a are used to classify the personal feature vector (107b).

Step 109 uses the output from step 108b to generate a corresponding diagnosis probability vector with multiple values associated with a patient's file, that provides a probability that the current subject has each condition analyzed, such that further diagnosis recommendations and treatment recommendations can be derived. Each value in the vector corresponds to one of the autoimmune conditions that the system is programmed to seek, with individual values representing the likelihood of the person having the associated autoimmune disease or condition. Usually, the system will compare these values to a threshold for exceeding or going below the pre-defined normal range, and when the threshold has been crossed, suggesting the possibility of a disease state, the system will generate an indication or alert. This process is explained in more detail in FIG. 6.

In the event that no diagnosis is made, step 109 may also provide output indicating the likelihood that the given individual may develop an autoimmune disease in the future.

Finally, in step 110, the doctor or other health care provider, generates retrospective feedback on the diagnostic accuracy of the output generated by the system. The physician's analysis of the system's performance is input to the expert medical logic database of step 102, to update and improve that data.

Figure 4:
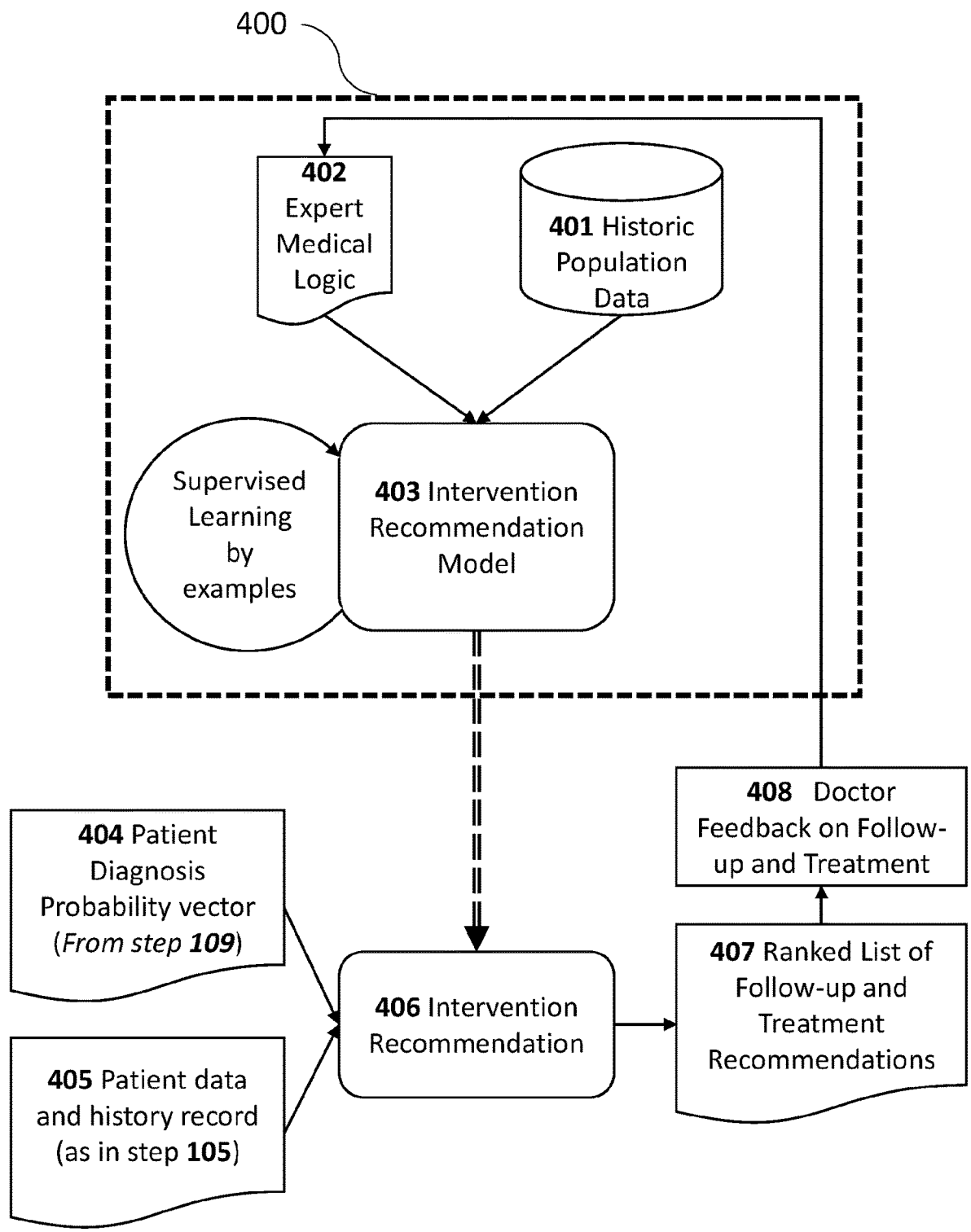
FIG. 4 depicts the flow and processing of information for intervention, treatment selection or therapeutic purposes in a representative implementation of the methods of the present disclosure.

In other implementations of the disclosed methods, the algorithm is able to provide from steps 109 and 110, treatment recommendations, referral suggestions, or follow-up advice, as will be further delineated in FIG. 4.

The following general CD parameters used for diagnosis, where CD is used as an exemplary disease for implementing this method, refer to the process described in FIG. 1. Example of parameters or features from the patient's data file, used in the machine learning algorithm may fall into the following categories: demographics including family history of CD or other gastrointestinal conditions, symptoms, concurrent diagnoses, lab tests, medications, procedure and current and past measurements such as height, weight, and BMI. A large number of parameters may be used in training the algorithm; over time, additional, different, or fewer parameters may be incorporated to improve the diagnostic accuracy of the method. Each of these categories are further defined and detailed below. Additional categories and additional parameters within each category may be included over time as the machine learning algorithm identifies and correlates other factors as having relevancy to the diagnosis of CD. Demographics includes gender, birth season, and age at the time of the test and, if known, age at the time of CD diagnosis.

Symptoms included are collected from the patient's historical data up to a predefined time window, before medical diagnosis of this condition actually took place for that patient. Specific relevant symptoms comprise those relating to abdominal pain; bloating (abdominal swelling); constipation; diarrhea; fatigue; headaches or migraines; weight loss; bone or joint pain; depression or anxiety; irritability and behavioral issues; peripheral neuropathy (tingling, numbness or pain in the hands and feet); seizures; skin rash; canker/ulcer sores inside the mouth; vomiting; pale, foul-smelling, or fatty stools; and acid reflux. Further symptoms may be included over time as the algorithm improves its specificity and accuracy, and is able to incorporate additional symptom patterns and correlate them with the diagnosis of CD.

Laboratory tests and measurements such as height, weight, and BMI include the minimum values, maximum values, and the first and last in the predefined time, e.g., 5 years, preceding the examination. For children, growth measurements over time are an important input to the system. The selected laboratory blood tests with relevance for diagnosis of CD are shown below, ALT (alanine aminotransferase, an indicator of liver damage); AST (aspartate aminotransferase, an indicator of liver damage); GGT (gamma-glutamyl transpeptidase); CRP (C-reactive protein); ESR (erythrocyte sedimentation rate); ferritin (a protein that stores iron in cells); folic acid; Hb (hemoglobin); MCV (mean corpuscular volume); RDW (red cell distribution width); HLA DQ2 and/or HLA DQ8. Also included in the category of laboratory tests are identification of anemia; size and volume of red blood cells; measuring enzymes responsible for liver function; and levels of vitamins in the blood, at least vitamin A; vitamin B12, and vitamin D. Further laboratory tests of the blood or other body fluids may be included over time as the algorithm improves its specificity and accuracy, and is able to incorporate additional lab values and correlate them with the diagnosis of CD.

Concurrent diagnoses associated with CD that may predispose to a diagnosis and are thus included in the algorithm include the following: acute gastroenteritis; attention deficit hyperactivity disorder (ADHD); alopecia (hair loss/baldness); anemia; aphthous stomatitis; autoimmune hepatitis; autoimmune thyroiditis (Hashimoto's disease); arthritis; infection with *Campylobacter jejuni* (a bacterium that causes inflammation of the bowel and diarrhea); dental enamel defects; dermatitis; herpetiformis enteritis due to rotavirus (a virus that causes severe diarrhea in children and infants); failure to thrive; giardiasis (a common parasitic disease manifested in diarrhea, abdominal pain, weight loss, vomiting, etc.); Helicobacter pylori infection of the gastric mucosa; herpetiformis dermatitis, a chronic skin disease manifested in blisters; IBD; infertility; recurrent miscarriage; missed menstrual periods; lactose intolerance; liver and biliary tract disorders (elevated transaminases, fatty liver, primary sclerosing cholangitis, etc.); osteoporosis or osteopenia; short statue; Type 1 diabetes; vitiligo; peripheral neuropathy (tingling, numbness or pain in hands or feet); skin and hair findings such as thin or damaged hair, brittle nails, or onychomycosis; autoimmune thyroiditis; and chronic hypertransaminasemia (elevated liver enzymes).

CD has a genetic component in that individuals with specific HLA alleles, i.e., DQ2 and DQ8, have an increased risk of developing CD (3% vs. 1% in the general population). Thus, the HLA haplotype for each individual may also be included as a parameter. Further diagnoses may be included over time as the algorithm improves its specificity and accuracy, and is able to incorporate additional results and correlate them with the diagnosis of CD.

Medications specifically included in the algorithm may include antibiotics (IV and PO); H2 receptor antagonists, which block histamines and remove acidity in the stomach; NSAIDs (nonsteroidal anti-inflammatory drugs); paracetamol; PPI (proton pump inhibitors, which inhibit acid secretion in the stomach); and steroids (IV and PO), which may damage the GI tract lining. Further medications and other routes of administration may be included over time as the algorithm improves its specificity and accuracy, and is able to incorporate additional findings and correlate them with the diagnosis of CD.

Objective measurements or values derived from measurements included in the algorithm include height (decrease in percentile, based on the z-score); weight; weight loss; BMI (either the numerical value, or a Boolean cutoff for normal); [current BMI]/[BMI when CD was diagnosed]; [current weight]/[weight when CD was diagnosed]; and [current height]/[height when celiac was diagnosed]. As with other parameter categories described above, further measurements may be included over time as the algorithm improves its specificity and accuracy, and is able to incorporate additional findings and correlate them with the diagnosis of CD.

In the initial iterations of the algorithm as it is being trained, inclusion criterion for subjects as having a diagnosis of CD can be based on the current standard of care for diagnosis of CD. The following section explains the procedures used in the use of expert medical logic and the tagging of CD patients based on the historic data, as implemented in step 304. The first level of diagnosis is a blood test called the tTG-IgA test, which detects antibodies to tissue transglutaminase. This test will be positive in about 98% of patients with celiac disease who are on a gluten-containing diet; results will be negative in about 95% of healthy people without CD, meaning that the results are not 100% accurate for either diagnosing or for ruling out a diagnosis of CD. The gold standard diagnostic tool is an endoscopic biopsy of the small intestine, which in positive cases shows inflammation and damage to the ciliated lining of the small intestine, leading to poor nutrient absorption. Results of the biopsy will be available in a subset of individuals having a positive tTG-IgA test, further confirming the diagnosis in those subjects. However, anyone with a positive tTG-IgA test will be considered to have CD, for the purposes of algorithm training. In cases where EMR data and lab test results are not available, use is made of medical diagnostic procedure codes from insurance or other claims indicating that the tTG-IgA test, or upper gastrointestinal endoscopy, has been performed; suspected medical diagnostic codes for celiac disease in more than one medical insurance claim are taken as an indication of a positive diagnosis of celiac disease.

Based on these initial results, subjects are divided into two groups. The treatment group is comprised of those individuals having a positive tTG-IgA test, or, in the event that there are no positive test results, similar indications mentioned above for insurance claims data; the control group is comprised of those having a negative tTG-IgA test result. Subjects who reach the diagnostic criteria for having CD are used to establish the 'ground truth', i.e., results of patients who have been historically diagnosed with CD. Ground truth refers to a dataset with accurate tagging that is used to train the model and test it, as the expected result is known to be accurate. In implementations of the present disclosure, ground truth is generated from the historic patient data files by identifying those files that have clear indication of positive diagnosis of specific diseases or clear indication of no disease. The system separates those files into data collected at a predefined time prior to the time of diagnosis and into target diagnosis tagging that embodies the correct diagnosis as later found for that subject.

In cases where specific diagnostic test results are not available, e.g. insurance claims without lab results, the 'ground truth' can be defined by identifying cases where a specific diagnosis of, for instance, suspected celiac disease, appears in the claims data at a later time after procedures or tests related to such a diagnosis have been performed. For example, claims for blood tests for tTG-IgA or gastro-endoscopy, followed later by claims including celiac diagnosis, would indicate that tests have had a positive outcome.

Figure 2:
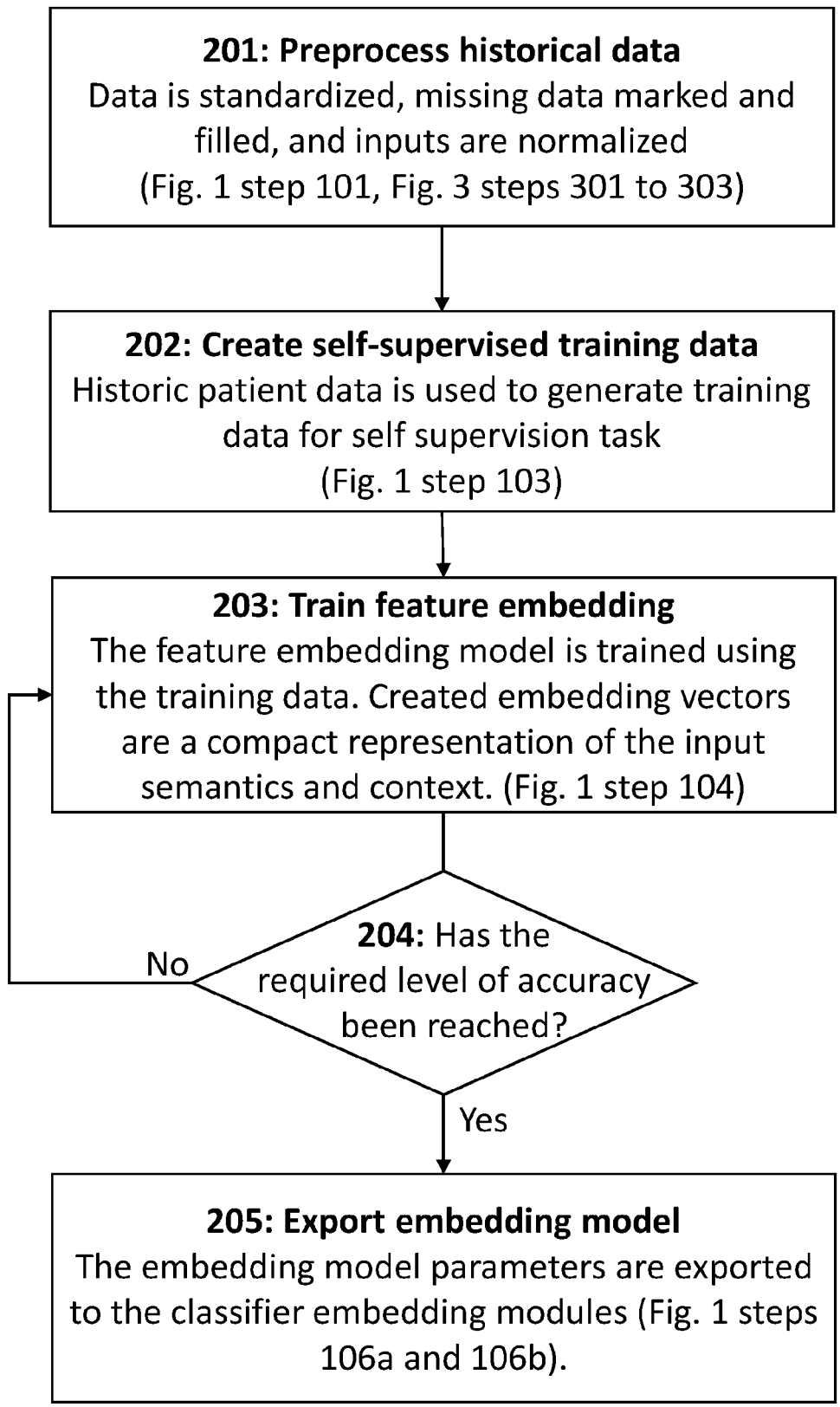
FIG. 2 is a flow chart detailing a high level algorithm description for steps 101 to 104 in FIG. 1.

FIG. 2 provides further details of the machine learning and other artificial intelligence procedures incorporated in the feature embedding model developed in steps 101 to 104 of FIG. 1.

In step 201, data are input from a large historic database of different medical, health and claims data collected per subject of a large population. These data are pre-processed to standardize, normalize and remove/fill missing values, a process that enhances the quality and quantity of information available to use for training, and upon which to base subsequent decisions.

In step 202, the input data is processed to generate training data for a self-supervised task. These tasks may include prediction of parts of the patient record based on another known part of that record, identifying randomly added, changed or removed data points in the medical record, or similar tasks that enable the model to learn a compact representation of the input data file via a smaller vector of real numbers. These patient data vectors are optimized in such a way that information located in proximity in the embedding space represents a similar level of risk with respect to the diagnostic probability of a given subject for developing the autoimmune disease under consideration.

In step 203, this embedding model is trained on a very large data set with self-supervised target outputs, its output providing the parameters for the embedding model. In other words, the embedding model transformation parameters are optimized so that the embedding vectors created will represent in a compact way the data features needed for diagnosis.

In step 204, the method determines if the required level of accuracy has been reached by measuring the accuracy achieved in the self-supervised training tasks. If not, the method returns to step 203 and refines the parameters with additional optimization cycles. If the required level of accuracy has been reached, the method proceeds to step 205, wherein the system exports the embedding model parameters to the classifier embedding modules in FIG. 1, steps 106a and 106b.

Figure 3:
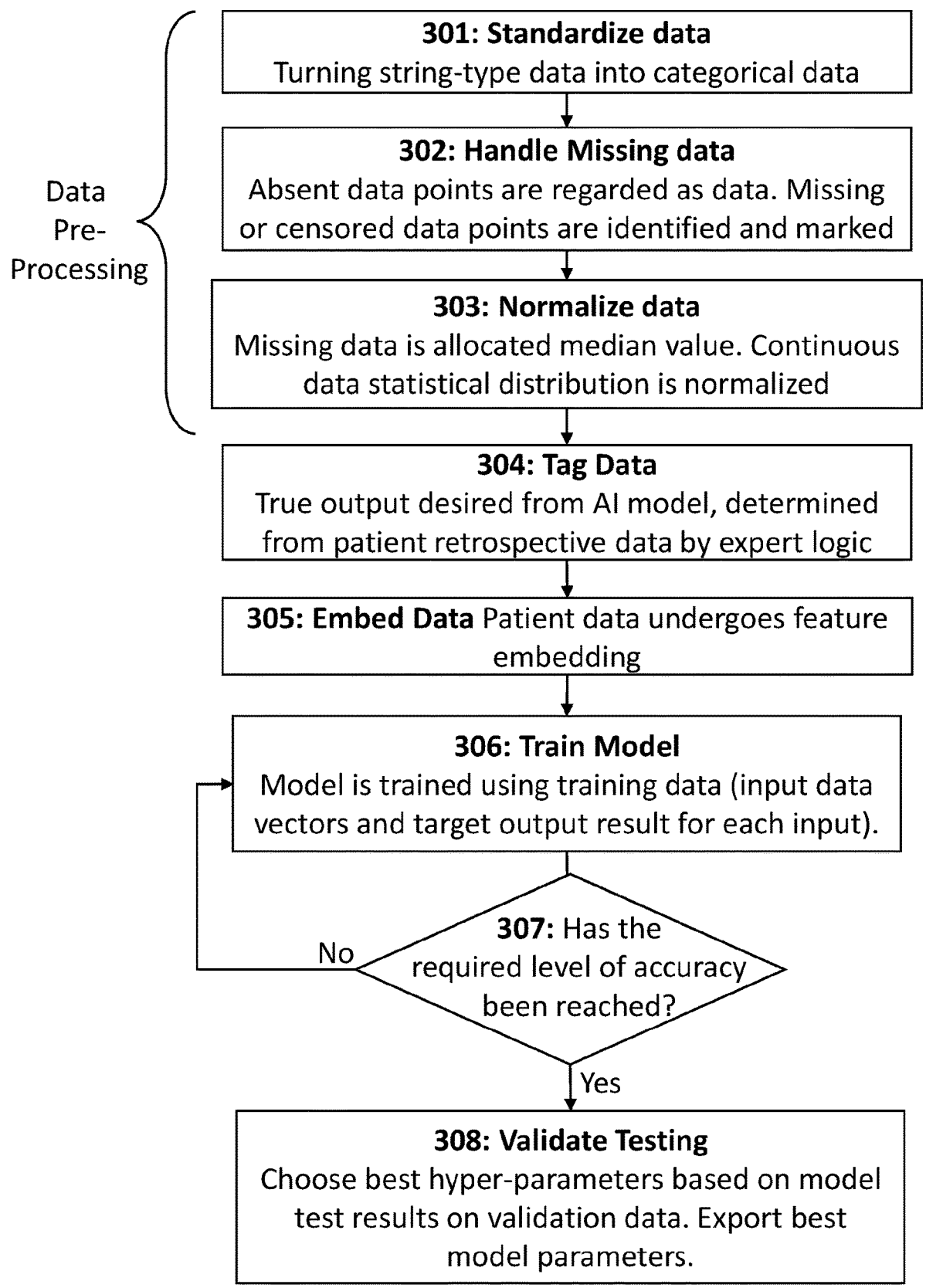
FIG. 3 is a flow chart detailing an exemplary high level algorithm description for celiac disease diagnosis, detailing a part of the flow chart of FIG. 1.

Reference is now made to FIG. 3, which explains the data handling procedures shown in the previous drawings in further detail, using an exemplary implementation of the method for predicting and diagnosing CD. The algorithm details sub-steps specifically for determining the probability of a given individual to have a positive transglutaminase antibody result indicating CD autoimmunity. It is to be understood that the same process may be applied to other medical data with predictive value for a given autoimmune disease, such as lab values, genetic biomarkers, or imaging studies.

Steps 301 to 303 delineate individual steps used in treatment of historical data from FIG. 1 step 101 and FIG. 2 step 201. Step 305 relates to the periodic training of the artificial intelligence model 100 in FIG. 1; similarly, the output of step 307 corresponds to the application of the multi-label classifier parameters derived in FIG. 1 step 108a to the individual subject data in step 108b.

In step 301, string-type data is standardized to categorical data. A string is a data type used in programming that is used to represent text rather than numbers, comprised of a set of characters. In this application, the word "autoimmune" and the phrase "gastrointestinal autoimmune disorder" are both strings. By contrast, categorical data have a limited, and usually fixed, number of possible values, e.g., assigning each individual to a particular group, such as "normal", "celiac disease", or "at risk for celiac disease", on the basis of the diagnosis probability vector. Data is collected from a source such as EMR, or from other sources such as a survey that is completed by the individuals or by an application such as the Apple Health App, which electronically collects health-related data from other applications and sources.

In step 302, each data point is annotated as present, missing or censored. Missing information is then used as data during the model learning by noting its absence in a separate feature and taking a median value for that data point from among all data sets in the relevant population, which comprises the data source. Features which comprise the algorithm inputs are determined, and cutoff values are selected for being outside the normal range and indicating a possible diagnosis of CD.

In step 303, all missing or censored data points are allocated the median of non-missing data points to complete the data set without changing its distribution. Features with continuous values (e.g. lab test numeric values) are normalized based on their common distribution in the population.

In step 304, which corresponds to step 103 of FIG. 1, the system uses expert medical logic to retroactively tag the historic data of each subject according to all autoimmune diseases that have been later diagnosed for this patient (based on more recent data collected). Using the diagnosis tagging, the system creates training vectors based on the historic data (prior to diagnosis), which, when added together with the correct diagnosis tagging, represents the desired classifier output.

In step 305, new subject data is entered and undergoes feature embedding. The embedding transformation converts the long vector of input features into a smaller embedding vector using the embedding model parameters from step 205. The results are training vectors, in which patients with similar conditions related to autoimmune diseases have similar vectors, making the training phase more efficient. An exemplary graph illustrating training vectors and new patient vectors is further delineated in FIG. 6.

In step 306, which corresponds to the periodic training steps, 100, of the artificial intelligence model in FIG. 1, the algorithm is trained and tested iteratively using supervised learning of the tagged training vectors and testing on the control group or validation set, as described in the periodic training steps of the artificial intelligence model 100 of FIG. 1, until the algorithm performs satisfactorily; the results should match the ground truth results according to the sensitivity and specificity pre-defined for the diagnosis classifier.

In step 307, the method determines if the required level of diagnostic accuracy has been reached; if not the method continues the supervised learning process of 306. If the required level of diagnostic accuracy has been reached, the method proceeds to step 308.

In step 308, the model is tested and validated using validation training samples set aside for the validation phase. The best model hyper-parameters, chosen to optimize the system performance using designated training vectors, are selected based on the validation set results, and the final performance evaluation is performed on a preselected test set. Hyperparameters, in machine learning, are structural parameters of the algorithm whose values are set before the learning process begins. By contrast, the values of other AI model parameters, sometimes called weights or factors in neural network architectures, are derived via training. Both of these types of 'parameters' are in distinction to the medical parameters or clinical features, referred to elsewhere in the present disclosure, that are used to define a subject's susceptibility or probability of developing a specific autoimmune disease.

Reference is now made to FIG. 4, a schematic representation of an implementation of the method for interventional recommendations. The steps within the dotted line 400 represent periodic training of artificial intelligence models. In block 403, an intervention recommendation model is developed, using supervised learning by examples. The training inputs for this model are examples generated from the population medical record database 401 using medical guidelines 402, and by collecting patients' response to specific treatments and scoring them accordingly. The information in steps 401 and 402 may be the same or different as that in FIG. 1 steps 101 and 102. These scores are used as target results to train the algorithm. After the model 400 is developed through machine learning or other form of artificial intelligence, the recommendation model parameters are input into the intervention recommendation model 406. Other inputs to the model 406 are the patient diagnosis probability vector from step 110 in FIG. 1, and patient historical data 405, comprised of previous tests and procedures, which may be the same data as provided in FIG. 1, step 105. The output of the intervention recommendation model is a ranked list of follow-up and/or treatment recommendations in step 407. Additionally, to the routine output in step 407, in step 408, the doctor or other health care provider can input retrospective feedback on the diagnostic accuracy of the output generated by the system. This information is used to improve the expert medical logic in step 402.

Figure 5:
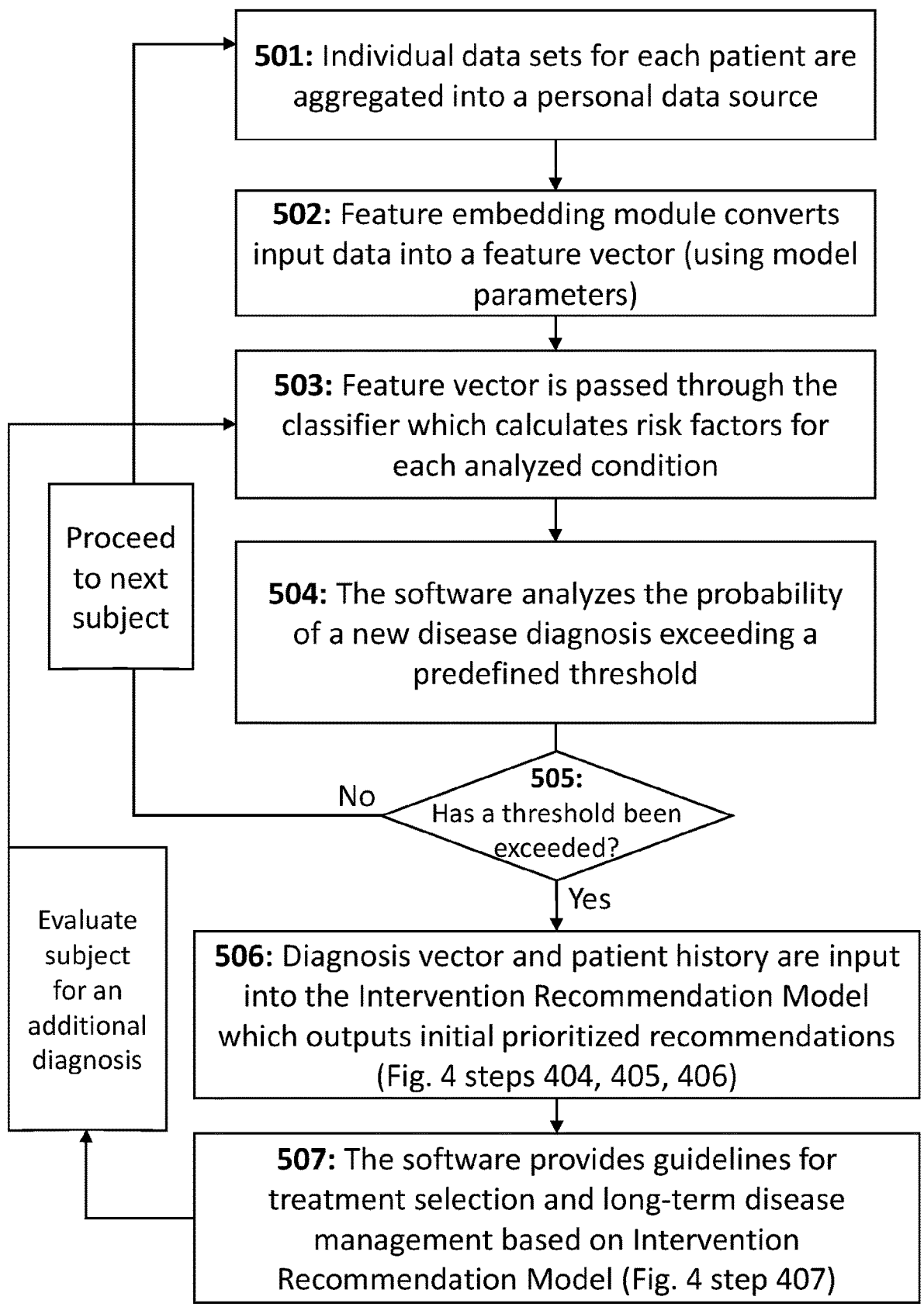
FIG. 5 is a flow chart detailing a high level algorithm for the treatment model of FIG. 4.

Reference is now made to FIG. 5, showing a description of how the algorithm operates within the full diagnostic system. Once the algorithm is fully trained and validated as described in FIG. 3, it may be used on other populations of undiagnosed individuals for screening and detection purposes. In this method, for the example of CD assessment, the algorithm calculates the probability of each given individual to have a positive TTG-IgA result, and notifies the software operator of cases reaching a specific threshold of probability, as described below. Image processing of small intestinal biopsy tissue slides from individuals with a high predictive probability of having or developing CD may be used to compare with images from individuals having previously been diagnosed with CD using small intestinal biopsy.

In step 501, individual data are aggregated into a personal patient data source. In step 502, the algorithm analyzes or processes each patient data set. In step 503, the algorithm calculates the probability of each subject having CD or other chronic, gastrointestinal autoimmune disease, by integrating the vectors for beyond-threshold values of any number of tests that fall outside the normal range. At this step, if active learning is used, the system may indicate need for additional medical information or request additional data from the subject. Active learning is a machine learning training method where the algorithm provides questions or suggests collection of additional data in order to improve its ability to provide specific and accurate diagnosis. The method analyzes the input patient vector to be classified, and if the vector falls in a "gray area" where the diagnosis is not clear, it will request additional information or data, such as for instance, a lab test result or a question to the subject about missing data. Following input of answers to these requests, the algorithm will be in a better position to provide a clear and more probable diagnosis.

In step 504, the system provides an alert when the probability of a given subject having one of the defined gastrointestinal autoimmune diseases, exceeds a predefined threshold. If the user requests more details, the system can provide explainability analysis of its decision, by means of identifying important parameters leading to its diagnosis decision. Explainability refers to mechanisms of analyzing the operation of machine learning, or other types of AI-based decision support algorithms, and presenting to the user how the recommendation has been reached and what parameters have most influenced this decision. The goal of these mechanisms is to build trust in the system's correctness by enabling an expert user to trace the decision factors and logic of the results and also enables effective human oversight of the process.

In step 505, the method determines whether a new diagnosis has been made. If not, the method proceeds to analyze the data of the next subject by returning to step 501. If a new diagnosis has been made, the method proceeds to step 506, in which the system provides initial guidelines for intervention selection among a group of available treatment options, and based on prior training of the algorithm for optimal outcomes. Such intervention may be based on novel therapies developed by third parties, which are expected to be developed over time. Thus, the system may be updated on a regular basis to incorporate the current standard of treatment for CD. Thus, the outcomes should continually improve over time. In step 507, the system provides guidelines for chronic disease supervision based on algorithm training. Such guidelines may provide short- or long-term follow-up recommendations, goals for exercise, diet, medical treatment, and other advice for successful long-term management of the condition and minimization of secondary complications.

The basis of personalizing the treatment selection is based on results of different patient subpopulations and groups, defined in more detail below. For example, lab results, concurrent diagnoses, and symptom clusters of CD patients tend to differ between adult and pediatric populations. Adults may have unexplained iron-deficiency anemia, fatigue, bone or joint pain, arthritis, osteoporosis or osteopenia (bone loss), liver and biliary tract disorders (transaminitis, fatty liver, primary sclerosing cholangitis, etc.), depression or anxiety, peripheral neuropathy (tingling, numbness or pain in the hands and feet), seizures or migraines, missed menstrual periods, infertility or recurrent miscarriage, canker sores inside the mouth, dermatitis herpetiformis (itchy skin rash). By contrast, pediatric patients may have a clinical picture that focuses more heavily on the gastrointestinal system and developmental issues. Patients may complain of abdominal bloating and pain; chronic diarrhea; vomiting; constipation; pale, foul-smelling, or fatty stools; weight loss; fatigue; irritability and behavioral issues; dental enamel defects of the permanent teeth; signs of malnutrition from lack of nutrient absorption such as delayed growth and puberty, short stature, and failure to thrive; and attention deficit hyperactivity disorder (ADHD).

The disclosed algorithm and system are able, via iterative processing and machine learning, to identify and distinguish between classical and non-classical presentations. In classical celiac disease, patients have signs and symptoms of malabsorption, including diarrhea, steatorrhea (pale, foul-smelling, fatty stools), and weight loss or growth failure in children. In non-classical celiac disease, patients may have mild gastrointestinal symptoms without clear signs of malabsorption or may have seemingly unrelated symptoms. They may suffer from abdominal distension and pain, and/or other indicators such as iron-deficiency anemia, chronic fatigue, chronic migraine, peripheral neuropathy (tingling, numbness or pain in hands or feet), unexplained chronic hypertransaminasemia (elevated liver enzymes), reduced bone mass and bone fractures, and vitamin deficiency (folic acid and B12), late menarche/early menopause and unexplained infertility, dental enamel defects, depression and anxiety, dermatitis herpetiformis (itchy skin rash), and other atypical clinical indicators, which may not be immediately associated with classical CD.

A further ability of the algorithm and system is to identify silent celiac, also known as asymptomatic celiac disease. Such patients are unaware of compromised digestive capacity and do not complain of symptoms, which may be mild, but nevertheless experience damage to their small intestine resulting in villous atrophy. Studies show that despite reporting no symptoms, after going on a strict gluten-free diet these individuals report better health and a reduction in acid reflux, abdominal bloating and distention and flatulence.

Figure 6:
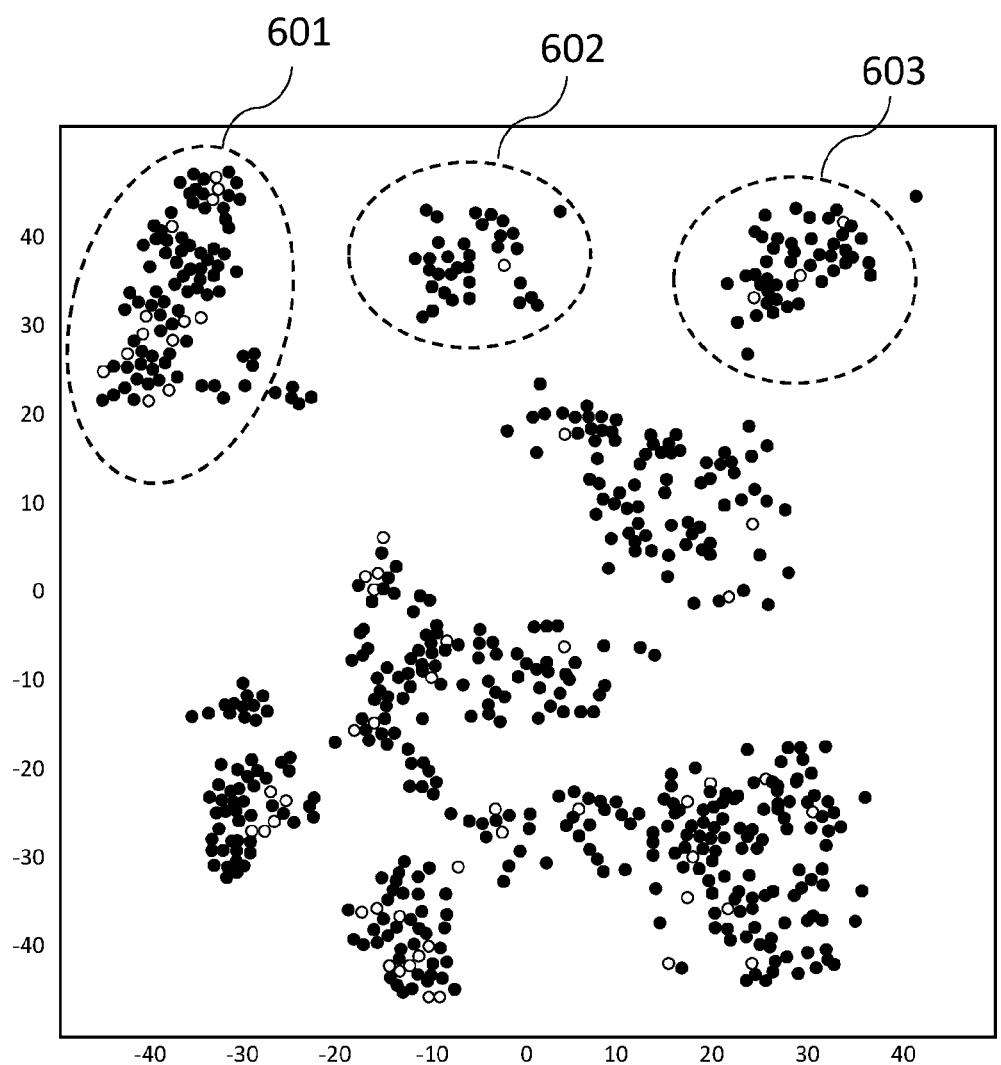
FIG. 6 is a visualization of embedding space, illustrating the clustering together of subjects with similar historic medical records, as created by the self-supervised training process of the feature embedding model.

Reference is now made to FIG. 6, showing a visualization of the embedding space, to illustrate the clustering of subjects with respect to lab values or other exemplary indicators of autoimmune disease. The data illustrate implementation of feature embedding, a machine learning method in which a large multi-dimensional set of features is converted into a smaller dimensional space containing the relevant information of the original data. In this example, feature embedding allows construction of a more efficient and accurate classifier for autoimmune diagnosis that generalizes from the reference population in which diagnoses of autoimmune diseases have been made, to as yet unseen new patient populations. The embedding vector captures semantics of the input by placing semantically similar inputs closer together in the embedding space, as illustrated and described below.

The graph is an output of the T-SNE (t-distributed stochastic neighbor embedding) algorithm, which is a dimensional reduction method that may be used to visualize data set clustering. Specifically, the algorithm takes high-dimensional data and visualizes them in a low-dimensional space of two or three dimensions. In this two-dimensional graph, the x- and y-axes represent transformed parameters that visually represent the similarities and dissimilarities between different inputs or points, each having a mean positioned at zero and deviations extending in both positive and negative directions from the mean. From these representations, it is possible to differentiate the clusters/groups and therefore predict, based on an individual subject's embedded feature vector, if he/she has or is likely to develop, a condition under consideration. The distribution in two dimensions of training data points for the transformed parameters in a given population is represented by black dots, whereas new patient data points are shown in empty dots, as explained further below. The larger, general population with normal values for the measured parameters are shown in the central-lower region of the graph, illustrating a range of normal values for the given parameters. By contrast, individuals diagnosed with a specific disease have values that differ significantly from normal and are part of the distinct clusters 601, 602, and 603 outlined by dotted ovals in the upper limits of the graph. These smaller disease clusters represent individuals having values that fall far from the mean average of normal individuals in the general population for the measured parameter on the y-axis, i.e., above the normal threshold. In terms of autoimmune disease, each small cluster may represent, for example, individuals identified as having or being predisposed to develop, CD 601, ulcerative colitis 602, or Crohn's disease 603. Thus, even though all of the individuals in these disease clusters have values outside—in this case, above—the normal threshold for the parameter measured on the y-axis, they vary among each other in terms of the second parameter represented on the x-axis, and each cluster or diagnosis can thus be distinguished from the others. In this example, the individuals in each disease cluster display values for the parameter represented on the x-axis which are below normal 601, normal 602, or above normal 603.

The new subjects' data points, shown as empty dots, appear throughout the parameter range and cluster together with similar subjects from the training set, so the classifier algorithm is able to use the clustering to suggest the correct diagnosis for such patients. The transformation of the feature vectors into the embedding space allows the system to predict or diagnose an individual at risk of a given autoimmune disease by placing this subject close to others with similar parameter values, i.e., sharing the same signs, symptoms, and other diagnostic criteria.

Individuals who have been screened and have a probability of CD diagnosis that is above normal but fails to reach threshold can be monitored with additional visits to follow the course of signs and symptoms over time, to determine whether the threshold is reached that would transfer the individual from the normal group to the treatment group.

Figure 7:
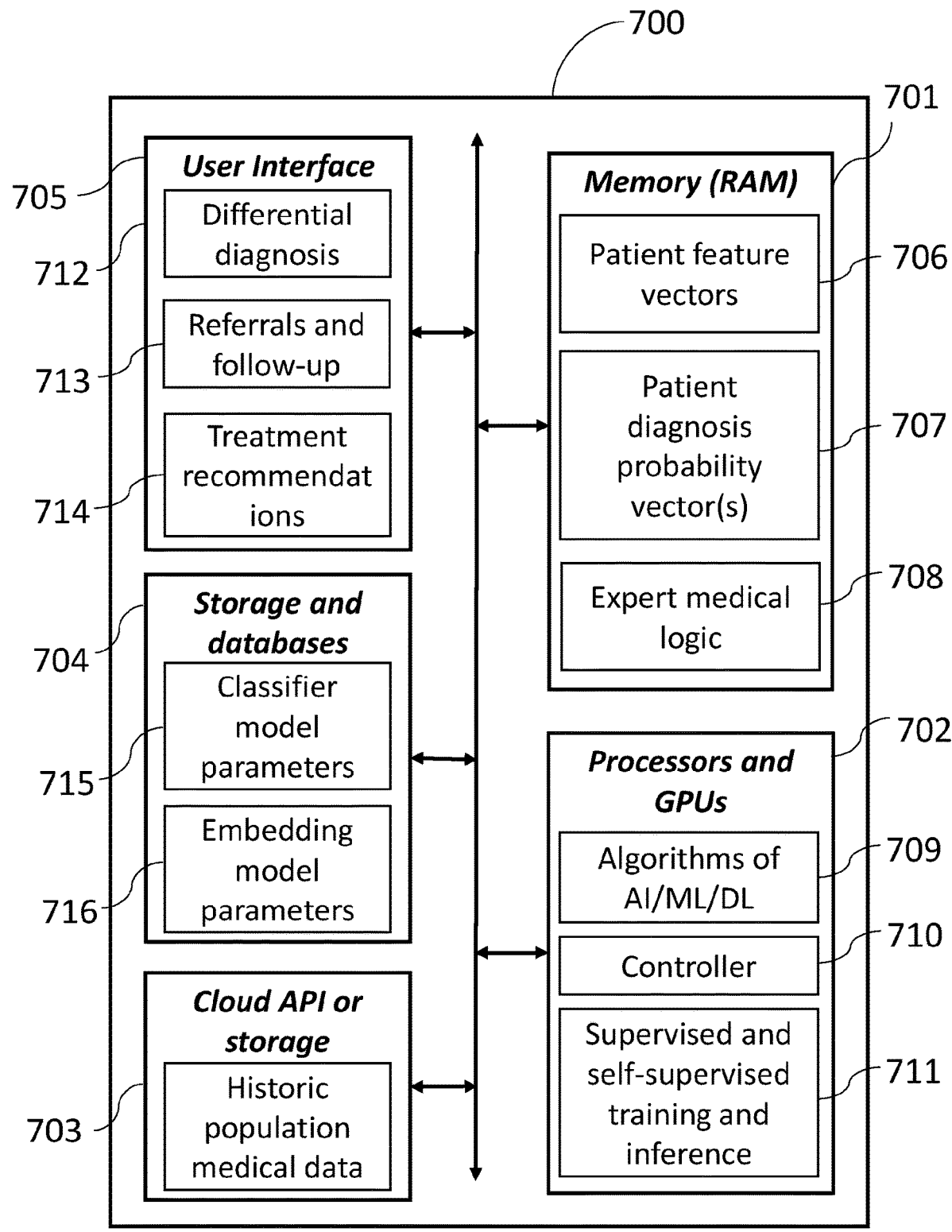
FIG. 7 shows an exemplary implementation of a system structure used to carry out the methods described in FIGS. 1 to 5.

Reference is now made to FIG. 7, showing a schematic representation of the system structure 700 used to perform the methods described herewithin above. In this disclosure, the term system may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array; at least one processor 702 (shared, dedicated, or group) that executes code; memory 701 (shared, dedicated, or group) that stores code executed by a processor 702; other suitable hardware components, such as optical, magnetic, or solid state drives, that provide the described functionality; or a combination of some or all of the above, such as in a system-on-chip.

The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this disclosure may be partially or fully implemented by one or more computer programs executed by one or more processors 702. The computer programs include processor-executable instructions that are stored on at least one non-transitory tangible computer readable medium, i.e., memory 701. The computer programs may also include and/or rely on stored data 703, 704.

In some implementations, the system comprises a memory 701, processors and graphic processing units 702, cloud application program interface or storage 703, other storage and databases 704, and a user interface 705. The components of the system 700 are further delineated below, with reference to the steps of the exemplary method in FIG. 1 to which they correspond. The memory 701 may comprise data relating to patient feature vectors 706 (FIG. 1, steps 106a, 106b), patient diagnosis probability vectors 707 (FIG. 1, step 109), and expert medical logic 708 (FIG. 1, step 102). The processing unit 702 may comprise algorithms of artificial intelligence, machine learning, and deep learning 709, a controller 710, and supervised and self-supervised training and inference 711 (FIG. 1, steps 103, 104, 106a, 106b, 108a, 108b). The cloud storage 703 may comprise historic population medical data (FIG. 1, step 101, 105). The at least one database 704 may comprise the data incorporating classifier model parameters 715 and embedding model parameters 716. The user interface 705 communicates with the medical staff or other professionals using the system, and provides the output of the system, such as a diagnosis or list of possible diagnoses, ranked in order of likelihood 712, referrals to specialists and follow-up guidelines 713, and in some implementations, treatment recommendations or guidelines 714.

In some implementations, the user interface is configured to communicate with other systems and share information via the IoT and other tools. The system may be configured to provide alerts to doctor or to insurer system or even to the subject via health app or other patient interface. Furthermore, the system may be configured to receive feedback from the user or a doctor regarding the accuracy of the classifier model results. Such human feedback regarding diagnosis or treatment/follow-up recommendations may be incorporated in order to influence future training cycles of its models, such as is shown in step 110 of FIG. 1 and 408 of FIG. 4.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

What is claimed is:

1. A method for predictive diagnosis of at least one autoimmune disease in a subject, comprising:
   (i) applying to health related data of the subject, a machine learning method adapted to convert parameters of the health related data, some of which may be indicative of a diagnosis of an autoimmune disease, into a vector that provides a compact representation of the health related data that reflects a medical condition of the subject; and
   (ii) applying a classifier model to the vector generated in step (i) to identify whether the medical condition of the subject indicates a likelihood of the subject having or developing an autoimmune disease,
   wherein the method comprises identifying the subject as having the likelihood of developing an autoimmune condition even when the subject is clinically asymptomatic;
   wherein the classifier model is generated by:
   (iii) accessing databases comprising records of health related data of a large population; wherein the records of health comprise electronic medical records (EMR), electronic heath records (EHR), insurance claims data and patient sensor data; wherein records of heath comprise structured data that is formatted to be searchable in relational databases, and unstructured data that lacks a pre-defined format or organization;
   (iv) tagging at least most of the records with information indicating if a member of the large population with whom a record is associated, has been diagnosed with an autoimmune disease;
   (v) performing the machine learning method, using self-supervised representation learning, on at least some of the tagged health related records, to convert tagged records into target diagnosis vectors indicating that the member associated with the tagged record has been diagnosed with an autoimmune disease; wherein the machine learning process is applied on tagged health related records that convey information about members only before the members were diagnosed with the autoimmune disease;
   (vi) training the classifier model iteratively to relate features of each target diagnosis vector with a previous diagnosis of an autoimmune disease by associating features of the target diagnosis vector representing the tagged records with the previous diagnosis of an autoimmune disease; and
   (vii) repeating the training until the associating features of the target diagnosis vector with the diagnosis of an autoimmune disease shows a desired level of accuracy, such that application of the classifier model to the vector generated in step (i) predicts with the desired level of accuracy, the likelihood that the subject has an autoimmune disease.

2. A method according to claim 1, wherein an autoimmune disease is at least one of a gastrointestinal autoimmune disease such as celiac disease, ulcerative colitis, or Crohn's disease.

3. A method according to claim 1, wherein the tagging comprises retroactively identifying and labeling each member medical history prior to the diagnosis of the member with autoimmune conditions that the member has been later positively diagnosed with.

4. A method according to claim 1, wherein the machine learning method is developed using self-supervised representation learning.

5. A method according to claim 4, wherein self-supervised representation learning uses a form of artificial intelligence.

6. A method according to claim 1, wherein the multi-class classifier model is developed using supervised learning.

7. A method according to claim 6, wherein supervised learning uses a form of artificial intelligence.

8. A method according to claim 1, wherein the accessing comprises using EMR-specific modular computer plugins for accessing the EMR, and providing access to doctors and policy makers to an output of step (ii) using an EMR's application programming interface.

9. A method according to claim 1, wherein tagging the records is performed using expert medical logic.

10. A method according to claim 1, wherein a database comprising records of health related data of a large population is used to generate the machine learning method.

11. A method according to claim 1, wherein the same database is used for generating both the machine learning method and the classifier model.

12. A method according to claim 1 further comprising generating an alert through electronic medical records regarding subjects with a risk factor above a pre-selected or automatically determined threshold.

13. A method according to claim 1 wherein the health related data of the subject is tagged and added to the database comprising records of health related data of the large population.

14. A method according to claim 9 wherein feedback from the health practitioner is appended into the expert medical logic to improve accuracy of the predictive diagnostic method.

15. A method according to claim 1, wherein the parameters are defined by current legacy methods based on a least one of published medical literature, diseases registries, medical practice guidelines and said medical data.

16. A method according to claim 1, wherein the health-related data comprises at least some of electronic medical or health records, the internet of things or other sensor data, health application data, and data from medical claims.

17. A method according to claim 1, wherein training the classifier model is performed using at least one of artificial intelligence, machine learning, deep learning, natural language processing, reinforcement learning, and big data analytics techniques.

18. A method according to claim 1, wherein the classifier model is a multi-label classifier model that outputs multiple results associated with the likelihood of the subject having more than one specific type of autoimmune disease or autoimmune related disease.

19. A method according to claim 1, further comprising: using supervised learning, training an intervention recommendation model to provide at least one of recommended intervention, treatment selection, disease management recommendations, and decision support guidelines.

20. A method according to claim 19, wherein the intervention recommendation model is trained by supervised learning from at least one of either the success or the effectiveness of interventions and treatments in the database comprising records of health related data of a large population.

21. A method according to claim 1, wherein the subject belongs to a subpopulation of the large population whose records of health related data comprise the database.

22. A method according to claim 1, wherein the health related data of the large population database are pre-processed by standardizing, marking and filling missing data points, and normalizing inputs.

23. A method according to claim 22, wherein the health related data of the large population database are used to create self-supervised training data.

24. A method according to claim 23, wherein the training data are used to train the machine learning method used to create embedding vectors that are a compact representation of the input semantics and context.

25. A method according to claim 1, wherein the health related data of the large population database are standardized by turning string-type data into categorical data.

26. A method according to claim 1, wherein missing data are handled by identification, marking, and filling in absent data points as actual data.

27. A method according to claim 26, wherein absent data points are allocated a median value, and the statistical distribution of continuous data is normalized.

28. A method according to claim 1, wherein optimal hyper-parameters are chosen and exported based on model test results on validation data.

29. A method according to claim 1, wherein the machine learning method is a feature embedding transformation.

30. A method according to claim 1, wherein the tagging of the records is also performed with information indicating with which autoimmune disease the member has been diagnosed.

31. A method according to claim 1, wherein application of the classifier model to the vector generated in step (i) predicts with the desired level of accuracy, the likelihood that the subject has a specific autoimmune disease.

32. A method according to claim 1, further comprising:
applying an intervention recommendation model to the patient diagnosis probability vector, if the subject is identified as having greater than a pre-defined likelihood of having or developing an autoimmune disease, wherein the intervention recommendation model is generated by:
a) accessing a database comprising records of health related data of members of a large population;
b) using expert medical logic to determine most effective treatment and follow up parameters of members of the large population who have been previously diagnosed with and treated for an autoimmune disease; and
c) training the intervention recommendation model iteratively to provide model parameters that meet accuracy requirements on test inputs, the model parameters provided by the intervention recommendation model being applied to the health related data of the subject and the patient diagnosis probability vector, to generate recommended interventions.

33. A system for predictive diagnosis of at least one autoimmune disease in a subject, comprising: at least one processor, a memory and at least one type of data storage;
wherein the at least one processor is configured to:
(i) apply to health related data of the subject, a machine learning method adapted to convert parameters of the health related data, some of which may be indicative of a diagnosis of an autoimmune disease, into a vector that provides a compact representation of the health related data that reflects a medical condition of the subject; and
ii) apply a classifier model to the vector generated in step (i) to identify whether the medical condition of the subject indicates a likelihood of the subject having or developing an autoimmune disease,
wherein the at least one processor is further configured to generate the classifier model by:
(iii) accessing databases comprising records of health related data of a large population; wherein the records of health comprise electronic medical records (EMR), electronic heath records (EHR), insurance claims data and patient sensor data; wherein records of heath comprise structured data that is formatted to be searchable in relational databases, and unstructured data that lacks a pre-defined format or organization;
(iv) tagging at least most of the records with information indicating if a member of the large population with whom a record is associated, has been diagnosed with an autoimmune disease;
(v) performing the machine learning method, using self-supervised representation learning, on at least some of the tagged health related records, to convert tagged records into target diagnosis vectors indicating that the member associated with the tagged record has been diagnosed with an autoimmune disease; wherein the machine learning process is applied on tagged health related records that convey information about members only before the members were diagnosed with the autoimmune disease;
(vi) training the classifier model iteratively to relate features of each target diagnosis vector with a previous diagnosis of an autoimmune disease by associating features of the target diagnosis vector representing the tagged records with the previous diagnosis of an autoimmune disease; and
(vii) repeating the training until the associating features of the target diagnosis vector with the diagnosis of an autoimmune disease shows a desired level of accuracy, such that application of the classifier model to the vector generated in step (i) predicts with the desired level of accuracy, the likelihood that the subject has an autoimmune disease;
wherein the at least one processor is configured to identify the subject as having the likelihood of developing an autoimmune condition even when the subject is clinically asymptomatic.

34. The system according to claim 33, wherein the at least one processor is further configured to provide at least one of recommended interventions, referrals to specialists, schedule of follow up testing, and a ranked list of treatment recommendations.

35. The system according to claim 33, wherein the artificial intelligence algorithms comprise a machine learning algorithm that was applied on tagged health related records that convey information about members only before the members were diagnosed with the autoimmune disease.

36. The system according to claim 33, further comprising a user interface that provides to a human operator at least one of recommended interventions, referrals to specialists, schedule of follow up testing, and ranked list of treatment recommendations.

37. The system according to claim 34, wherein recommended interventions include health-promoting activities such as diet or exercise, and treatment recommendations include drugs or other chemical therapies.

* * * * *